(12) United States Patent
Steiner (10) Patent No.: US 10,708,478 B2
(45) Date of Patent: Jul. 7, 2020

(54) IMAGE TRANSFORMATION AND DISPLAY FOR FLUORESCENT AND VISIBLE IMAGING

(71) Applicant: KARL STORZ Imaging, Inc., Goleta, CA (US)

(72) Inventor: Michael Steiner, Goleta, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 949 days.

(21) Appl. No.: 15/078,276

(22) Filed: Mar. 23, 2016

(65) Prior Publication Data
US 2017/0280029 A1   Sep. 28, 2017

(51) Int. Cl.
*H04N 5/232* (2006.01)
*H04N 5/225* (2006.01)
(Continued)

(52) U.S. Cl.
CPC ........ *H04N 5/2256* (2013.01); *A61B 1/0005* (2013.01); *A61B 1/00009* (2013.01); *A61B 1/043* (2013.01); *A61B 5/0035* (2013.01); *A61B 5/0071* (2013.01); *A61B 5/0084* (2013.01); *A61B 8/5261* (2013.01); *G06T 11/001* (2013.01); *H04N 7/183* (2013.01); *H04N 9/64* (2013.01); *A61B 5/0066* (2013.01); *A61B 5/0086* (2013.01); *A61B 8/12* (2013.01); *A61B 2576/00* (2013.01); *G02B 23/2461* (2013.01); *G02B 23/2484* (2013.01); *G06T 2210/41* (2013.01); *H04N 5/2258* (2013.01); *H04N 2005/2255* (2013.01)

(58) Field of Classification Search
CPC ... A61B 1/00009; A61B 1/0005; A61B 1/043; A61B 2576/00; A61B 5/0035; A61B 5/0066; A61B 5/0071; A61B 5/0084; A61B 5/0086; A61B 8/12; A61B 8/5261; G02B 23/2461; G02B 23/2484; G06T 11/001; G06T 2210/41; H04N 2005/2255; H04N 5/2256; H04N 5/2258; H04N 7/183; H04N 9/64
USPC .......................................................... 348/68
See application file for complete search history.

(56) References Cited

U.S. PATENT DOCUMENTS

3,712,199 A * 1/1973 Songer, Jr. ......... G02B 27/2207
                                                      352/60
6,091,400 A * 7/2000 Halls ...................... G09G 5/02
                                                     345/602
(Continued)

*Primary Examiner* — Jonathan R Messmore
(74) *Attorney, Agent, or Firm* — The Culbertson Group, P.C.; Michael Loi (57) ABSTRACT

Improved fluoresced imaging (FI) and other sensor data imaging processes, devices, and systems are provided to enhance display of different secondary types of images and reflected light images together. Reflected light images are converted to a larger color space in a manner that preserves the color information of the reflected light image. FI or secondary images are transformed to a color range within the larger color space, but outside the color area of the reflected light images, allowing the FI or secondary images to be combined with them in a manner with improved distinguishability of color. Hardware designs are provide to enable real-time processing of image streams from medical scopes. The combined images are encoded for an electronic display capable of displaying the larger color space.

25 Claims, 7 Drawing Sheets

(51) Int. Cl.
*A61B 1/04* (2006.01)
*A61B 1/00* (2006.01)
*A61B 8/08* (2006.01)
*H04N 7/18* (2006.01)
*G06T 11/00* (2006.01)
*A61B 5/00* (2006.01)
*H04N 9/64* (2006.01)
*G02B 23/24* (2006.01)
*A61B 8/12* (2006.01)

(56) References Cited

U.S. PATENT DOCUMENTS

| | | | | |
|---|---|---|---|---|
| 8,600,159 B2* | 12/2013 | Greenebaum | ............ | H04N 9/67 382/167 |
| 8,706,184 B2* | 4/2014 | Mohr | ............ | G06T 5/50 600/407 |
| 9,055,862 B2* | 6/2015 | Watanabe | ............ | A61B 1/00009 |
| 9,179,042 B2* | 11/2015 | Atkins | ............ | G06T 5/007 |
| 9,521,395 B2* | 12/2016 | Shintani | ............ | H04N 13/239 |
| 2001/0009269 A1* | 7/2001 | Hayashi | ............ | A61B 1/00009 250/458.1 |
| 2011/0164127 A1* | 7/2011 | Stehle | ............ | A61B 1/00009 348/65 |
| 2011/0261175 A1* | 10/2011 | Fomitchov | ............ | A61B 5/0071 348/61 |
| 2011/0292178 A1* | 12/2011 | Goma | ............ | H04N 13/128 348/46 |
| 2012/0268573 A1* | 10/2012 | Schonborn | ............ | A61B 1/051 348/49 |
| 2013/0250062 A1* | 9/2013 | Tin | ............ | G06T 7/85 348/46 |
| 2014/0333660 A1* | 11/2014 | Ballestad | ............ | G09G 5/00 345/593 |
| 2015/0062153 A1* | 3/2015 | Mihalca | ............ | A61B 1/04 345/604 |
| 2018/0025477 A1* | 1/2018 | Min | ............ | G06T 5/00 345/590 |
| 2018/0270474 A1* | 9/2018 | Liu | ............ | G06K 9/00201 |

\* cited by examiner

IMAGE TRANSFORMATION AND DISPLAY FOR FLUORESCENT AND VISIBLE IMAGING

TECHNICAL FIELD OF THE INVENTION

The invention relates generally to the field of image capture and more specifically to a medical imaging camera systems and methods which combine fluorescent imaging with visible color imaging.

BACKGROUND OF THE INVENTION

Endoscopes and other medical scopes often use fluorescing agents or autoflorescence to better examine tissue. A fluorescing agent such as a dye may be injected or otherwise administered to tissue, and then an excitation light is directed toward the tissue. When the excitation light is removed, the fluorescing agent fluoresces (emits light typically at a higher wavelength than the excitation light), allowing a sensor to detect the light, which is often not in a wavelength visible to the human eye. The detected light is formatted to images, and examining the images can indicate the concentration of fluorescing agent in the observed tissue. Further, a phenomenon known as autoflorescence may occur in which tissue fluoresces light under certain conditions without a fluorescing agent. Such light can be detected as well. Images based on detected fluoresced light, known as "fluorescence imaging" (FI), are therefore useful in medical diagnosis, testing, and many scientific fields.

Other medical sensing schemes such as ultrasonic or optical coherence tomography also produce data represented to the user as images. It is often necessary to display visual color images of along with the FI or other sensor images in order to properly distinguish features and determine all desired characteristics of the tissue being investigated. The visual color images are produced by emitting light toward the tissue, and with a camera, or image sensor, taking pictures of the reflected light. Both the reflected light images and FI images can be put into image streams to show a video of the two images to the user such as a doctor using a FI endoscope.

Systems are also known which combine or overlay FI images with reflected light images of the same area to help users interpret the data in both images, such as to identify cancerous tissue. For example, U.S. Pat. No. 9,055,862 to Watanabe et al. discloses a fluorescence imaging processing device that combines a FI image with a return-light image, and processes the images with various exponential functions based on distance. Another document, U.S. Publication No. 2011/0164127 by Stehle et al. describes a method for showing endoscope images with fluorescent light. In this case, the fluoresced light is at visible wavelengths in the RGB color space and is detected with a visible light camera. The method seeks to enhance the fluoresced light portion of the image non-linearly by processing it to enhance the variations in the fluorescent light while de-enhancing the variations in other parts of the image's RGB color space. Another method for combining FI and reflected light images is found in U.S. Pat. No. 8,706,184. In this method, the visible light image is "desaturated", that is the colors are changed to be less colorful, and in some cases the colors are completely desaturated into grey scale images. The FI image is superimposed with the desaturated image so that fluorescent features may be clearly seen relative to the more grey version of the reflected light image. All of these techniques, and others like them, suffer from distortion of colors in the reflected light image and difficulty in distinguishing FI image features when combined with the reflected light image.

What is needed are improved ways to process and display fluoresced light-based images or other medical images with visible color images. What is further needed are systems that can process a stream of images from both secondary sensors and reflected light and combine them in a manner that improves lag time in processing the image streams through the image processing device.

SUMMARY OF THE INVENTION

It is an object of the invention to provide improved display of fluorescence imaging (FI) images or other sensor-based images, and reflected light images, through a systems and methods that preserve the color information of the reflected light image while allowing FI or other images to be combined with in a manner with improved distinguishability of colors. This has the advantage of improving the distinguishability of features in both images, and thereby further enhancing the analytical or diagnostic benefits of providing a combined image. It is another object of the invention to provide system designs, image processing circuit designs, image processing methods and digital signal processor or graphics processing unit program code, that can process a stream of images from both FI and reflected light and combine them with the improved display techniques herein in a manner that improves lag time in processing the image streams through the image processing device.

According to a first aspect of the invention, an imaging scope system is provided for producing both reflected light image streams and FI image stream. The system includes a light source configured to direct visible light and fluorescent excitation light toward a subject scene. An optical assembly is configured to direct received light from the subject scene toward an image sensor assembly. The image sensor assembly includes a sensor array capable of detecting visible light. It may also detect fluoresced light with the same sensor, or have one or more additional fluoresced light sensor arrays. The image sensor assembly detects first fluoresced light from the subject scene and produces at least one output signal response. From the sensor the detected light signals are passed to image forming circuitry configured to receive the detected signals and produce a first image stream including reflected light images having a first color space, the range of colors that can be shown by the form of the image stream, and a second image stream representing the first fluoresced light.

These image streams are fed to image processing circuitry that, when operated, performs several steps to prepare and combine the images so a user can see the FI and reflected light images together. The image processing circuitry converts the format of the first image stream into a second data format having a second color space larger than the first color space, while the conversion preserves the color space content of the first image stream. The image processing circuitry also formats the second image stream to the second data format, and transforms the second image stream to a first color range inside the second color space and outside the first color space. It combines the converted first image stream and the transformed second image stream and produces a combined image stream. The combined image stream is fed to video encoder circuitry configured to encode the combined image stream to a video encoding format configured for display on an electronic display capable of displaying the second color space. The system may include the display as well, configured to display the larger color space.

In some implementations, the first image stream forms the first color space with a first bit depth, the number of bits used per primary color, and the converted image stream forms the second color space with a second bit depth larger than the first bit depth. Transforming the second image stream to a first color range may include mapping an intensity, or brightness, range in the second image stream to an intensity range of a selected color. In other versions, intensity in second image stream may be mapped to a range of colors. The first fluoresced light may be from an indocyanine green (ICG) fluorescing agent, and the first color range displaying it may be green or multiple shades of green, yet not the same greens as may be expressed in the reflected light image. In another version, the first fluoresced light may be from an an indocyanine green (ICG) fluorescing agent, and the first color range displaying it may consists essentially of shades of green, shades of blue, or shades of both green and blue. In some versions, the second image stream has a bit depth expressing intensity variation of the detected first fluoresced light, this bit depth being smaller than the bit depth of the second color space. The image processing circuitry can transform such a second image stream to the second color space by adding an intensity variation in the second image stream to a base value for a single selected color in the second color space.

Some version of the imaging scope system can detect second fluoresced light at a spectrum different from that of the first fluoresced light, and produce a second fluoresced light signal in response. In these cases, the image forming circuitry is further configured to produce a third image stream representing the second fluoresced light, and the image processing circuitry is further configured to format the third image stream to the second data format and transform the third image stream to a second color range inside the second color space and outside the first color space, and also outside the first color range showing the first fluoresced imagery. The spectrum of the second fluoresced light may be ultraviolet. The system then combines the third image stream with the first and second image streams.

In some implementations, the image processing circuitry further includes first processing circuitry for processing the first image stream and second processing circuitry operating in parallel with the first processing circuitry for processing the second image stream, the first and second processing circuitry both connected to image combining circuitry. These parallel circuits may be programmable logic circuits in a field programmable gate array (FPGA). Other versions may use one or more graphics processing units (GPUs) or other digital signal processors (DSPs) executing program code programmed according to methods herein. Converting the format of the first image stream may be done by accessing a lookup table containing a set of first pixel values for pre-converted first images and an associated set of second pixel values for converted second images. Or, it may be done by calculation circuitry multiplying the image pixel values with matrices designed to change the format to the second color space.

The first color space may an 8-bit color space, with the second color space a BT-2020 compliant 10-bit or 12-bit color space, where the combined image stream is encoded to a BT-2020 compliant video format and fed to a display controller for transmission to the display. The system may include a display, which is preferably a 4K or other UHD monitor or television configured to display the 10-bit or 12-bit color space discussed above as defined by the BT-2020 ITU recommendation. The use of such a display together with a visible image stream of 8-bit color depth allows display of the second image stream (FI images) in a color format with a color range "far away" or visually distinguishable from colors present in the first image stream. It also allows for a similar transformation process to add a third FI image stream to be combined with the first visible color image stream and the second FI image stream, which can also be presented "far away" in the color space from the first and second image streams to improve visual distinguishability of features for the users.

According to a second aspect of the invention, a method of transforming information representing detected light is provided. The method includes receiving a first image stream produced from detected visible light and formatted in a first bit depth expressing a first color space of visible light. It also receives a second image stream produced from detected first fluoresced light. It then converts the format of the first image stream into a second color space format having a second bit depth larger than the first bit depth, the second color space larger than the first color space, while preserving color space content of the first image stream. The method also transforms the second image stream to a portion of the second color space outside the first color space, and combines the converted first image stream and the transformed second image stream into a combined image stream and encodes the combined stream formatted for a display capable of displaying the second color space. Because the color range employed for the transformed second image stream is outside the preserved color range for the visible images, the two can be overlaid to provide improved visibility of colors in the original visible image stream. Further, this technique reduces color distortion in the visible image stream when combining with the transformed second image stream. The processing steps in method may be encoded as program code for an image processor, or designed into circuitry, or some combination of the two.

In some implementations of the second aspect, transforming the second image stream to a first color range comprises mapping an intensity range in the second image stream to an intensity range of a selected color. Transforming the second image stream to a first color range inside the second color space and outside the first color space may be done by mapping an intensity range in the second image stream to the first color range. The first fluoresced light may be from an indocyanine green (ICG) fluorescing agent, and transforming the second image stream map transform to a color range consisting of a green color or multiple green colors. Transforming the second image stream may be done by adding an intensity variation in the second image stream to a base value for a single selected color in the second color space, where the bit depth of the second image stream is also smaller than the second bit depth.

Additional implementations of the second aspect include processing another FI image stream for combination with the first two image streams. This includes receiving a third image stream produced from detected second fluoresced light at a spectrum different from that of the first fluoresced light, then formatting the third image stream to the second data format and transforming the third image stream to a second color range inside the second color space and outside the first color space, and outside the first color range used for the first FI image stream. The transformed third image stream is then combined with the first and second image streams. Some implementations of the second aspect may include detecting the reflected and fluoresced light and producing the various image streams therefrom.

According to some implementations of the second aspect, first color space is an 8-bit color space and the second color space is a BT-2020 compliant 10-bit or 12-bit color space, and encoding the combined image stream includes encoding to a BT-2020 compliant video format. Converting the format of the first image stream may be done by accessing a lookup table containing a set of first pixel values for pre-converted first images and an associated set of second pixel values converted second images. Also, transforming the second image stream may be done by accessing a lookup table containing a set of input pixel values for pre-transformed second images and an associated set of output pixel values for transformed second images. Transforming from second image stream further comprises adding a transparency level to the second image stream, used in combining the converted first image stream and the transformed second image stream using alpha blending in which the transparency level is alpha level for the second image stream. The third image stream may be similarly alpha blended with its own transparency value. These alpha values may be a user-adjustable value.

According to a third aspect of the invention, a method of transforming information representing detected sensor data is provided. The method includes receiving a first image stream produced from reflected light and formatted in a first bit depth expressing a first color space of visible light. It also includes receiving a second image stream produced from a second sensor having an angle of sensing at least substantially shared with an angle of view of the first image stream. It then converts the format of the first image stream into a second color space format having a second bit depth larger than the first bit depth, the second color space larger than the first color space, while preserving color space content of the first image stream. The method also transforms the second image stream to a portion of the second color space outside the first color space, and combines the converted first image stream and the transformed second image stream into a combined image stream and encodes the combined stream formatted for a display capable of displaying the second color space. Because the color range employed for the transformed second image stream is outside the preserved color range for the visible images, the two can be overlaid to provide improved visibility of colors in the original visible image stream. Further, this technique reduces color distortion in the visible image stream when combining with the transformed second image stream. The processing steps in method may be encoded as program code for an image processor, or designed into circuitry, or some combination of the two.

According to some implementations of the third aspect, the second sensor data is received from one of an ultrasonic sensor, an infrared sensor, or a near-infrared sensor. Some versions may employ optical coherence tomography to produce the second sensor data. According to some implementations, a second emitter or scope assembly is provided, and may be integrated into the same scope housing as a scope detecting the visible light, or may be in a separate detachable housing constructed to be attached and detached by a user.

According to a fourth aspect of the invention, a camera control unit (CCU) is configured to receive a first image stream including visible light images having a first color space and a second image stream representing detected fluoresced light. The CCU includes image processing circuitry configured to (a) convert a format of the first image stream into a second data format having a second color space larger than the first color space, while preserving color space content of the first image stream; (b) format the second image stream to the second data format and transform the second image stream to a first color range inside the second color space and outside the first color space; and (c) combine the converted first image stream and the transformed second image stream to produce a combined image stream. The camera control unit may further include video encoder circuitry configured to encode the combined image stream to a video encoding format configured for display on an electronic display capable of displaying the second color space.

Implementations of the first aspect of the invention are also implementable according to the forth aspect of the invention (e.g., the various configurations and functionalities of image processing and video encoding circuitry). Implementations of the forth aspect may include the CCU performing the method steps according to the second aspect of the invention.

Implementations of the invention may also be embodied as software or firmware, stored in a suitable medium, and executable to perform various versions of the methods herein. These and other features of the invention will be apparent from the following description of the preferred embodiments, considered along with the accompanying drawings.

DETAILED DESCRIPTION OF EXAMPLE EMBODIMENTS

The invention provides improved display of fluorescence imaging (FI) images or other sensor-based images, and reflected light images, through a systems and methods that preserve the color information of the reflected light image while allowing FI or other images to be combined with in a manner with improved distinguishability of colors. This has the advantage of improving the distinguishability of features in both images, and thereby further enhancing the analytical or diagnostic benefits of providing a combined image. Also provided are system designs, image processing circuit designs, image processing methods and digital signal processor or graphics processing unit program code, that can process a stream of images from both FI or a secondary sensor, and reflected light and combine them with the improved display techniques herein in a manner that improves lag time in processing the image streams through the image processing device. The techniques and features herein may also be embodied in or used to process images from other types of image capture devices such as fluorescent microscopes.

Because digital cameras and FI sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 1:
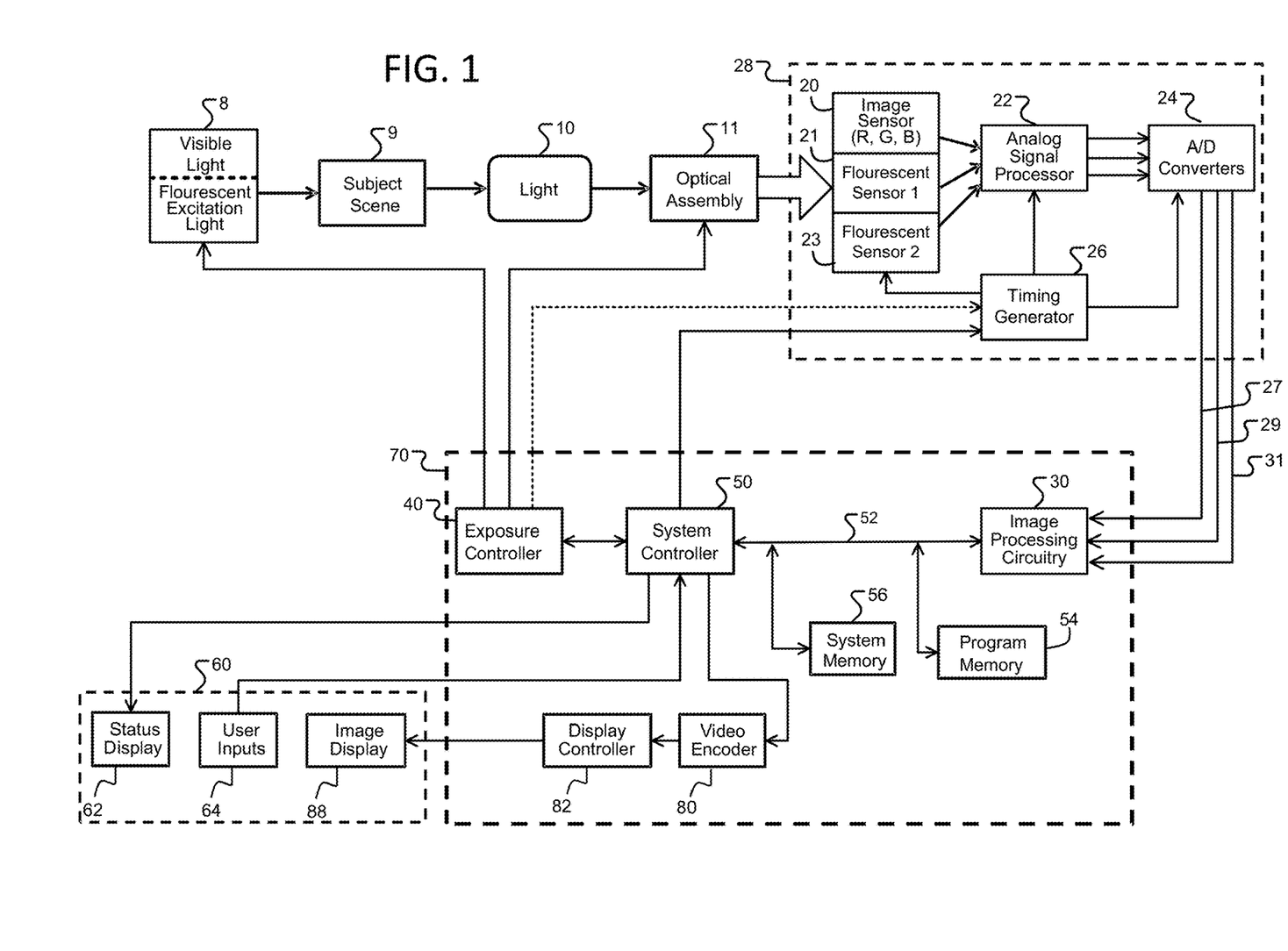
FIG. 1 is a hardware block diagram of an example image capture device according to an example embodiment of the invention.

Referring to FIG. 1, a block diagram of an image capture device according to an example embodiment of the invention is shown. The invention is clearly applicable to more than one type of device enabled for image capture, such as endoscopes incorporating solid state image imagers, digital microscopes, digital cameras, mobile phones equipped with imaging sub-systems, and automotive vehicles equipped with imaging sub-systems, for example. A light source 8 illuminates subject scene 9 with visible light and fluorescent excitation light, which may be outside the visible spectrum in the ultra-violet range or the infra-red/near infrared range, or both. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser LEDs positioned toward the front of the scope. Any suitable known elements for emitting visible and fluorescent excitation light may be used elements for the light emitting elements included in light source 8. As shown in the drawing, light 10 reflected from (or, alternatively, as in the case of fluorescence, transmitted by) the subject scene is input to an optical assembly 11, where the light is focused to form an image solid-state image sensor 20 and fluoresced light detectors 21 and 23, which are all sensor arrays responsive to a designated spectrum of light.

In this version, multiple sensor arrays are employed for visible light and for fluoresced light which may include visible and invisible spectrums. In some versions, a single image sensor 20 may be employed, configured as a sensor array having a spectral range of sensitivity covering visible light, near infra-red, and ultra violet light. If multiple fluorescent imaging (FI) schemes are employed, the image sensor may include a separate image sensor constructed to receive the specific wavelengths fluoresced in the various FI techniques used. The depicted sensors include two different fluoresced lights sensors 21 and 23 that sense fluoresced light in the invisible ranges of IR (fluorescent sensor 1) and ultraviolet (fluorescent sensor 2). Optical assembly 11 includes at least one lens, which may be a wide-angle lens element such that optical assembly 11 focuses light which represents a wide field of view. Image sensor 20 and fluoresced light sensors 21 and 23 converts the incident visible and invisible light to an electrical signal by integrating charge for each picture element (pixel). The image sensor 20 and fluoresced light sensors 21 and 23 of the preferred embodiment may be active pixel complementary metal oxide semiconductor sensor (CMOS APS) or a charge-coupled device (CCD). The total amount of light 10 reaching the image sensor 20 and fluoresced light sensors 21 and 23 is regulated by the light source 8 intensity, the optical assembly 11 aperture, and the time for which the image sensor 20 and fluoresced light sensors 21 and 23 integrate charge. An exposure controller 40 responds to the amount of light available in the scene given the intensity and spatial distribution of digitized signals corresponding to the intensity and spatial distribution of the light focused on image sensor 20 and fluoresced light sensors 21 and 23. Exposure controller 40 also controls the emission of fluorescent excitation light from light source 8, and may control the visible and fluorescent light emitting elements to be on at the same time, or to alternate to allow fluoresced light frames to be captured in the absence of visible light if such is required by the fluorescent imaging scheme employed. Exposure controller may also control the optical assembly 11 aperture, and the time for which the image sensor 20 and fluoresced light sensors 21 and 23 integrates charge. The control connection from exposure controller 40 to timing generator is shown as a dotted line because the control is typically indirect. Typically exposure controller 40 has a different timing and exposure scheme for each of sensors 20, 21, and 23. Due to the different types of sensed data, the exposure controller 40 may control the integration time of the sensors 20, 21 and 23 by integrating sensor 20 at a fixed 60 Hz or 50 Hz frame rate (standard frame rates for USA versus European video, respectively), while the FI sensors 21 and 23 may be controlled to vary their integration times in several different frames rate modes (it shall be variable anywhere from 1 Hz to 200 Hz). The frame rate of sensor 20 will typically govern the synchronization process such that images frames based on sensors 21 and 23 are repeated or interpolated to synchronize in time with the 50 or 60 fps rate of sensor 20.

Analog signals from the image sensor 20 and fluoresced light sensors 21 and 23 are processed by analog signal processor 22 and applied to analog-to-digital (A/D) converter 24 for digitizing the analog sensor signals. The digitized signals each representing streams of images or image representations based on the data, are fed to image processor 30 as image signal 27, first fluorescent light signal 29, and second fluorescent light signal 31. Image processor 30 includes circuitry performing digital image processing functions as further described below to process and combine visible light images of image signal 27 with the fluoresced light data in signals 29 and 31. It is noted that while this version includes two different fluoresced light schemes, other versions may use only one, and some may use more than two including three, four, or more different fluoresced light imaging techniques.

Timing generator 26 produces various clocking signals to select rows and pixels and synchronizes the operation of image sensor 20, analog signal processor 22, and A/D converter 24. Image sensor assembly 28 includes the image sensor 20, the analog signal processor 22, the A/D converter 24, and the timing generator 26. The functional elements of the image sensor assembly 28 can be fabricated as a single integrated circuit as is commonly done with CMOS image sensors or they can be separately-fabricated integrated circuits.

The system controller 50 controls the overall operation of the image capture device based on a software program stored in program memory 54. This memory can also be used to store user setting selections and other data to be preserved when the camera is turned off. System controller 50 controls the sequence of data capture by directing exposure controller to set the light source 8 intensity, the optical assembly 11 aperture, and controlling various filters in optical assembly 11 and timing that may be necessary to obtain image streams based on the visible light and fluoresced light. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). For each fluoresced light signal (29, 31) to be processed and displayed by the system, the GUI presents at least one control or adjusting the transparency of the false-color fluoresced light image when blended with the systems visible light images, as further described below. The GUI typically includes menus for making various option selections.

Image processing circuit 30 is one of three programmable logic devices, processors, or controllers in this embodiment, in addition to a system controller 50 and the exposure controller 40. Image processing circuit 30, controller 50, exposure controller 40, system and program memories 56 and 54, video encoder 80 and display controller 82 may be housed within camera control unit (CCU) 70. CCU 70 may be responsible for powering and controlling light source 8, image sensor assembly 28, and/or optical assembly 11.

Although this distribution of imaging device functional control among multiple programmable logic devices, programmable logic devices, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

Figure 2:
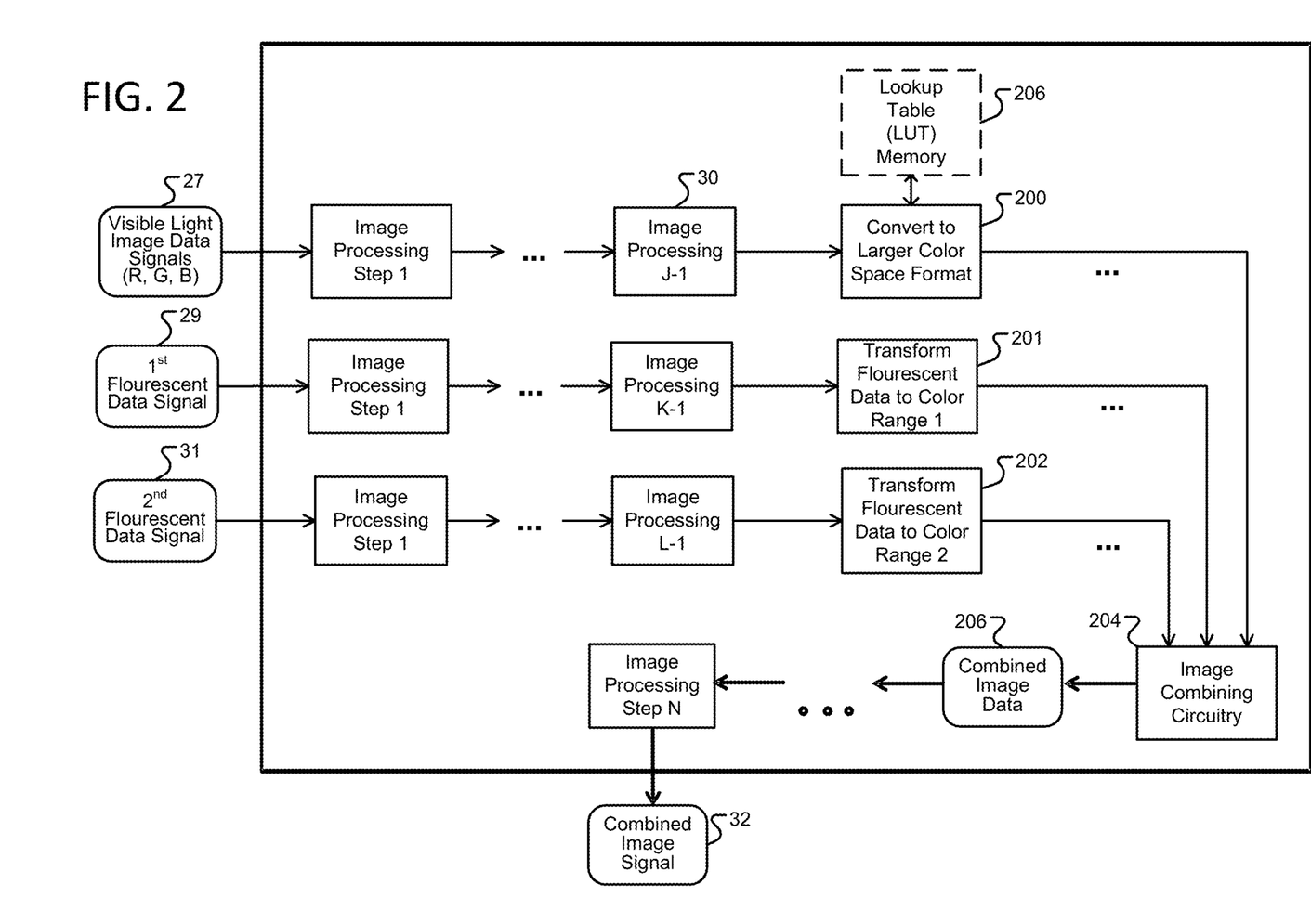
FIG. 2 is a block diagram showing more of the image processing circuitry of FIG. 1.

FIG. 2 shows in more detail the example image processing circuit 30 from FIG. 1, which performs digital image processing functions to process and combine visible light images of image signal 27 with the fluoresced light data in signals 29 and 31 to produce the desired form of image from the data received. Image processing circuit 30 generally performs several image processing steps on the image frames in signals 27, 29, and 31, reflected in the depicted sequence. Image signal 27 with the fluoresced light data in signals 29 and 31 are shown being fed to image processing circuit 30 on the left. For image signal 27, circuitry for performing zero or more image processing steps precede the conversion to the larger color space at circuitry block 200, which performs the integer number Jth processing step. The processing of block 200 converts the format of the image stream of image signal 27 from an original, first color space (preferably an 8-bit depth for each primary color, using primaries as defined in the BT-709 recommendation) into a new, second, data format (typically a 10-bit or 12-bit depth for each primary color, using primaries as defined in the BT-2020 recommendation) having a larger color space than the first color space, while preserving color space content of the first image stream. That is, the colors in the first image stream are kept the same despite a reformatting to a larger color space expressed with more bit depth and different primary colors. Circuit block 200 may access local lookup table (LUT) memory 208, or a LUT in system memory 56. Format conversion may be conducted with a LUT or directly calculated with a matrix multiplication of the RGB values in the first color stream. The processing of circuitry 200 will be further described below. Circuitry for performing zero or more image processing steps may follow the conversion to the larger color space at block 200 before performing the image combining circuitry 204, which produces an image stream of combined image data 206 showing a visible combination of the data signals 27, 29, and 31. Zero or more steps follow the image combining circuitry 204 to produce the final combined image signals 32. Similarly, for fluoresced data signals 29 and 31, circuitry for performing zero or more image processing steps precede the transformation of each signal to the second color space at circuit blocks 201 and 202. Block 201, which is an integer number Kth step of processing signal 29, formats the image stream represented by fluoresced data signal 29 to the second data format and transform the image stream to a first color range inside the second color space and outside the first color space. Block 202, which is an integer number Lth step of processing signal 31, formats the image stream represented by fluoresced data signal 31 to the second data format and transform the image stream to a second color range inside the second color space and outside the first color space, and also outside the first color range used for the transformed image stream of signal 29. The transformation of signals 29 and 31 as well as the characteristics and design considerations for the various color spaces involved will be further described below, but may also involve local memory accessing a LUT (not shown) for each conversion. Further processing steps may be performed by additional circuit blocks following blocks 200, 201, and 202, and preceding the imaging combining process performed at block 204. The further processing steps are preferably independent and may vary depending on the type of FI imaging employed, the application, user settings, and various other design considerations. After block 204, data bus 52 transports the exposure level signals 202 to the system controller, or directly to the exposure controller 40, and transfers other information both ways between the system controller 50 and each of the image processing steps. The transported information typically includes image processing step parameters and user-selected option indicators.

In the illustrated embodiment, image processing circuit 30 manipulates the digital image data according to processes that are either programmed into the circuit (in the case of programmable logic devices) or loaded into the circuit program memory as programming instructions (in the case of processors and controllers such as a graphics processing unit (GPU)). The digital image data manipulation includes, but is not limited to, image processing steps such as color filter array demosaicing, noise reduction, color correction, image unwarping, and gamma correction. The image processing may further include frame syncing in designs where the frame rate of signals 29 and 31 are lower than that of signal 27. For example if signal 27 includes 30 frames-per-second color images, but signal 29 has a longer sensor integration time and only contains 5 or 10 frames-per-second of fluoresced light data, image processing circuitry may need to hold, repeat, or interpolate frames between blocks 201 and 204 in order that the image combining process performed by block 204 is properly synced. In this version the digital image data manipulation performed by image processing circuit 30 also includes and calculating control signals from each signal 27, 29, and 31 such as exposure levels required by exposure controller 40 to adjust the imaging device for proper light levels in the detected light.

The various depicted circuitry blocks inside image processor 30 are preferably FPGA logic blocks inside a single FPGA device, which includes an on-chip controller and memory. However, this is not limiting and processors, ASICs, GPUs, and other suitable circuits may be used to implement the depicted circuitry blocks.

Figure 3:
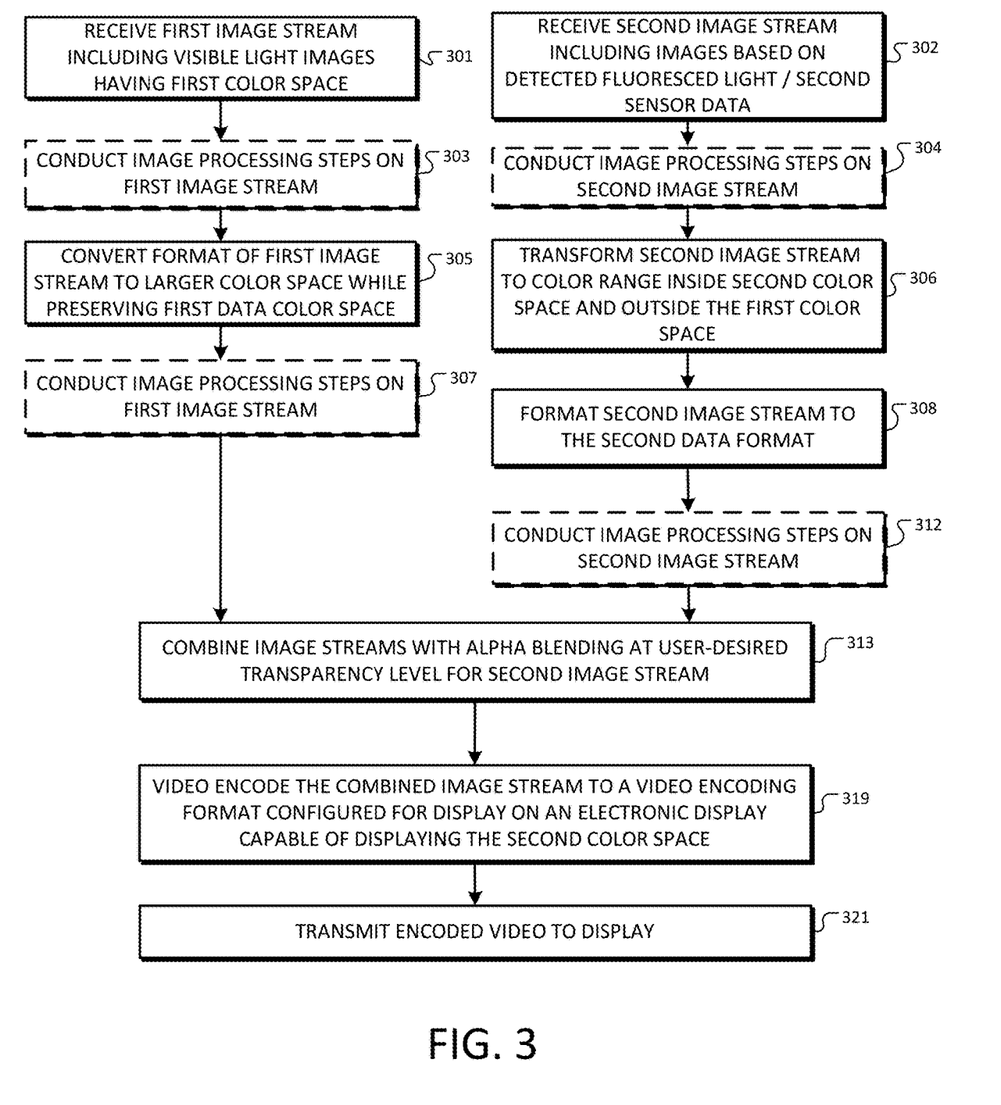
FIG. 3 is a flowchart of a fluorescent image and visible image display process according to some embodiments.

FIG. 3 is a flowchart of a combined color and fluoresced imaging process according to some embodiments, which may be employed with the example hardware and functional designs of FIGS. 1-2, or may be employed with other hardware designated with a similar purpose, such as software program code executed by a GPU or other image processor. Generally, the process shows a method of transforming information representing detected light. At process block 301 includes receiving a first image stream, such as that in data signal 27 (FIG. 2), produced from detected visible light and formatted in a first bit depth expressing a first color space of visible light. In the presently preferred embodiment, the color space is defined an 8-bit depth for each primary color, using R, G, and B primaries as defined in the BT-709 recommendation. Other versions may use other bit depths, such as, for example, older sensor output formats that used 6 bits per color channel, or 7 or 9 bits, and other primary color definitions to define the first color space. Further the first color space may be a 10-bit or larger color space as long as the second color space has a larger format to accommodate the insertion of FI signals as discussed below. The first color space is preferably defined by at least three primaries. Table 1 below defines the color space used in the BT-709 recommendation, used in this example as the first color space and employing an 8-bit depth per primary.

TABLE 1

BT-709 Color Space Definition

| | White Point | | Primaries | | | | | |
|---|---|---|---|---|---|---|---|---|
| | $x_W$ | $y_W$ | $x_R$ | $y_R$ | $x_G$ | $y_G$ | $x_B$ | $y_B$ |
| ITU-RBT.709 | 0.3127 | 0.3290 | 0.64 | 0.33 | 0.30 | 0.60 | 0.15 | 0.06 |

Figure 5:
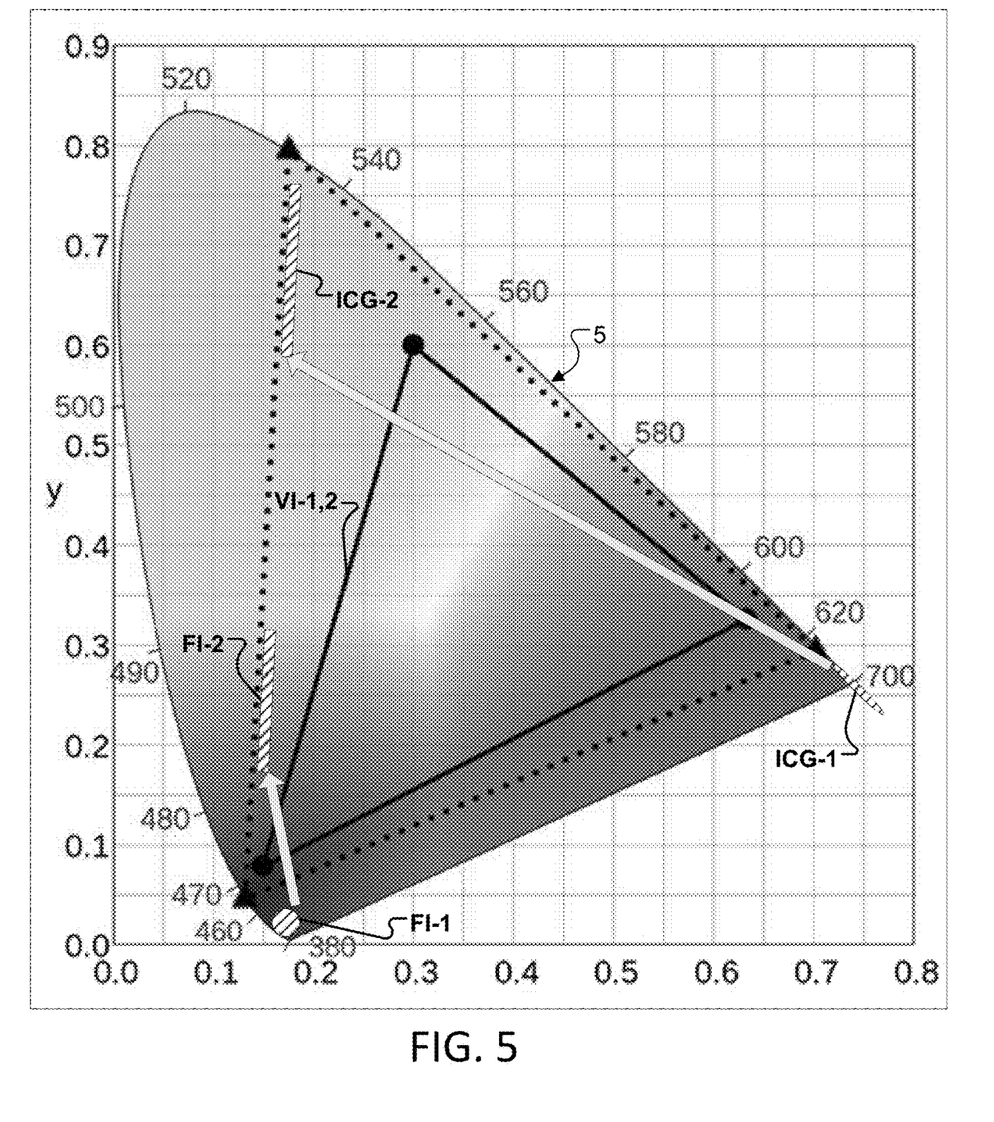
FIG. 5 shows an example color space diagram according to an embodiment in which two FI image signals are transformed to different color ranges having color variation therein.

FIG. 5 shows an example color space diagram according to an embodiment in which the BT-709 8-bit per channel RGB color space is employed for the first image stream. The diagram is a CIE 1931 color space chromaticity diagram, with y parameter expressing a measure of the color's brightness or luminance, x expressing a measure of the human eye's response to colors, and the color's chromaticity being expressed as a function of the two parameters x and y. The CIE visible light diagram shows the area of colors visible to the human eye by the curved boundary, marked with arrow 5, which denotes pure wavelength light, with wavelengths shown in nanometers. Drawn onto the chromaticity diagram is a solid triangle marked VI-1,2, which shows the color space of the first image stream, which is the same color space defined by the bit depth and primaries of the first image stream. The remaining parts of the diagram, and another embodiment shown in FIG. 6, will be discussed below.

To prepare the first image stream received at block 301 for combination with FI imagery and display, the process at block 303 conducts one or more image processing steps, with block 303 shown in dotted lines to indicate it is optional in some embodiments. Next at block 305, the process converts the format of the first image stream from an original, first color space into a new, second, data format (typically a 10-bit or 12-bit depth for each primary color, using primaries as defined in the BT-2020 recommendation) having a larger color space larger than the first color space, while preserving color space content of the first image stream. The color spaces should be chosen such that the conversion does not cause significant rounding or conversion artifacts if the second color space does not have enough color resolution to closely recreate the colors from the original color space in the new color space. Since the second color space is larger and has more colors to express, at least a two bit difference in bit-depth is recommended. That is, the colors in the first image stream are kept the same despite a reformatting to a larger color space expressed with more bit depth and different primary colors. This result is depicted in FIG. 5, with the second color space shown by the dotted triangle depicting the 10-bit color space using primaries as defined in the BT-2020 recommendation. While the first image stream data format is changed to the larger triangle, but the color space is not expanded so the colors in the first image stream remain unchanged at the original, smaller color space labeled VI-1,2. The format conversion at block 305 may be conducted with a lookup table (LUT) or directly calculated with a matrix multiplication of the RGB values in the first color stream. The second colors space is preferably defined by at least three or four primaries. One version converts the RGB values in the first color stream from a three-primary format to a four-primary format, such as modern display formats using a yellow primary to enlarge the display color space. The preferred version uses a three-primary color space as the second, larger, color space. When using a matrix for the conversion, the conversion matrix may be constructed using a matrix converting the first color space, such as BT-709, to the CIE 1931 XYZ color space, multiplied by an inverse matrix to convert from the XYZ space to the second, larger color space, such as the BT-2020 color space defined in Table 2 below. Both color spaces employ the same white point in this example.

TABLE 2

BT-2020 Color Space Definition

| | White Point | | Primaries | | | | | |
|---|---|---|---|---|---|---|---|---|
| | $x_W$ | $y_W$ | $x_R$ | $y_R$ | $x_G$ | $y_G$ | $x_B$ | $y_B$ |
| ITU-RBT.2020 | 0.3127 | 0.3290 | 0.708 | 0.292 | 0.170 | 0.797 | 0.131 | 0.046 |

To preserve the white point of the original color data if the second color space format uses a different white point than the first, a suitable chromatic adaptation transform such as the Bradford transform may be employed in creating the matrix. The resulting conversion matrix may be employed on the RGB values in each pixel of the first image stream. The same effect may be achieved with a LUT based on the desired conversion matrix applied to pixel values to create the table, which typically uses more memory but may be faster than calculated conversion depending on the circuit design employed.

Referring again to the process of FIG. 3, in parallel to processing of the visible light images starting at block 301, the right-hand branch of the flowchart shows the fluoresced light-based images being processed. At block 302, the process receives a second image stream produced from detected first fluoresced light. A third image stream may also be processed similarly to the second image stream, as discussed above with respect to the second fluorescent data signal 31. Optional image processing steps are conducted at block 304 before the transformation. At block 306, the process transforms the second image stream to a portion of the second color space outside the first color space. One example of this transformation is depicted on the diagram of FIG. 5, where a depicted area showing fluoresced indocyine-green light spectrum is shown at signal ICG-1, the light being detected and stored typically as intensity values interpreted as a grayscale image stream or FI image, even though all or some of the detected light in many embodiments is not actually visible light. The FI image stream containing signal ICG-1 is shown being transformed as depicted by the arrow to a portion ICG-2 of the second color space, which is outside the first color space. This allows the image of the fluorescent data to be displayed combined or overlaid with the visible color image, without requiring a change to the color space content of the color image itself. Transforming the second image stream may be done by accessing a lookup table containing a set of input pixel values for pre-transformed second images and an associated set of output pixel values for transformed second images. Transforming the second image stream may also be done by a transform algorithm executed by a processor or digital logic. Such an algorithm may include intensity to color transformation and intensity scaling as discussed above. Transforming the second image stream may also be done based on user configurable values for transparency, brightness, color, color range beginning, and color range end, for example. Transforming from second image stream may also include adding a transparency level to the second image stream, where combining the converted first image stream and the transformed second image stream further comprises alpha blending in which the transparency level is used as the alpha level for the second image stream.

Next at block 308, the process formats the transformed image stream to the second data format, the same format used for the first stream. This process block may occur simultaneously with or before block 306. Further image processing may be conducted at block 312 before the image streams are combined.

The combining occurs at block 313, which combining the converted first image stream and the transformed second image stream into a combined image stream and transmitting the combined stream encoded for a display capable of displaying the second color space. The combination may be done by overlaying or alpha blending the images, or other suitable means of image combining. In a preferred version, the block 313 includes adding a transparency level to the second image stream, which may be set by the user through the user interface. Then combining the converted first image stream and the transformed second image stream is done by alpha blending in which the transparency level is used as the alpha level for the transformed second image stream. Because the color range employed for the transformed second image stream is outside the preserved color range for the visible images, the two can be overlaid to provide improved visibility of colors in the original visible image stream. Further, this technique reduces color distortion in the visible image stream when combining with the transformed second image stream.

Next at block 319, the process video encodes the combined image stream to a video encoding format configured for display on an electronic display capable of displaying the second color space. Preferably such display is a 4K or other UHD monitor or television configured to display the 10-bit or 12-bit color space discussed above as defined by the BT-2020 ITU recommendation. Block 321 then transmits this encoded signal for display on such a display. The use of such a display together with a visible image stream of 8-bit color depth allows display of the second image stream (FI images) in a color format with a color range "far away" or visually distinguishable from colors present in the first image stream. It also allows for a similar transformation process to add a third FI image stream to be combined with the first visible color image stream and the second FI image stream, which can also be presented "far away" in the color space from the first and second image streams to improve visual distinguishability of features for the users.

Figure 4:
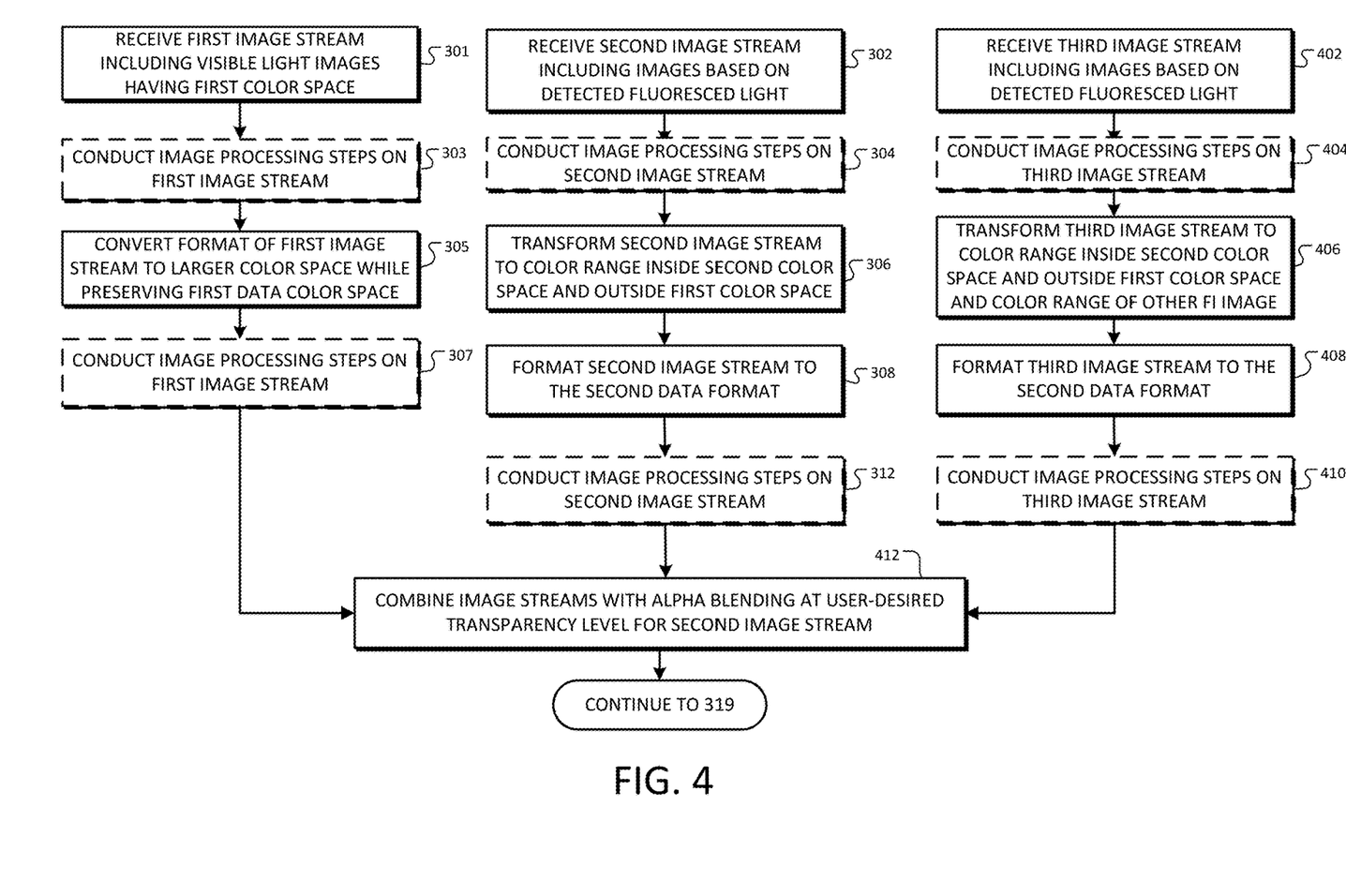
FIG. 4 is a flowchart of a process combining three image streams according to some embodiments.

FIG. 4 is a flowchart of a process for combining a third image stream according additional embodiments of the invention. The flowchart steps for the first two image streams are similar to those described above with respect to FIG. 3, and have the same numbering. The process for handling the third image stream begins at block 402. The process may include emitting excitation light and detecting the fluoresced light of the second image stream, using hardware such as that described with respect to FIG. 1, or may include a process conducted on a camera control unit including image processing circuitry 30 and system controller 50, the process beginning with receiving the image streams from a scope device including image sensor assembly 28. Referring to FIG. 4, the third image stream received at block 402 will typically be based on FI data from an FI scheme complimentary or different to the FI scheme used for the second image stream. Block 402 receives a third image stream produced from detected second fluoresced light at a spectrum different from that of the first fluoresced light. In the example of FIG. 5, the second image stream represents IR fluoresced light (such as from an ICG fluoresced imaging method) shown at ICG-1 and transformed to the color range ICG-2. The third image stream in this example is a based on detected ultra-violet fluoresced light shown on the color diagram at FI-1, which is transformed at block 406 (FIG. 4) to a second color range FI-2, inside the second color space and outside the first color space, and outside the first color range. Transforming the third image stream may be done by accessing a lookup table containing a set of input pixel values for pre-transformed second images and an associated set of output pixel values for transformed third images. Transforming the third image stream may also be done by a transform algorithm executed by a processor or digital logic. Such an algorithm may include intensity to color transformation and intensity scaling as discussed above. Transforming the third image stream may also be done based on user configurable values for transparency, brightness, color, color range beginning, and color range end, for example. Transforming from second image stream may also include adding a transparency level to the second image stream, where combining the converted first image stream and the transformed second image stream further comprises alpha blending in which the transparency level is used as the alpha level for the second image stream. In the version of FIG. 5, the second color range includes blues selected from the blue end of the color space. However this is not limiting and other ranges may be selected from the area outside the first color space and inside the second color space.

Next at block 408, the process formats the third image stream to the second data format. As with the process of FIG. 3, the reformatting and transformation of blocks 406 and 408 (and blocks 306 and 308) may occur together in an image processing step or may occur in any order. Further image processing may occur on the reformatted third image stream at block 410. Then at block 412, the image streams are combined similarly to the process described for block 313. The combination may occur with a single operation on all three streams or first combining any two and then combining the remaining stream with the combined stream. The process then continues to encoding and display at step 319 of FIG. 3.

Figure 6:
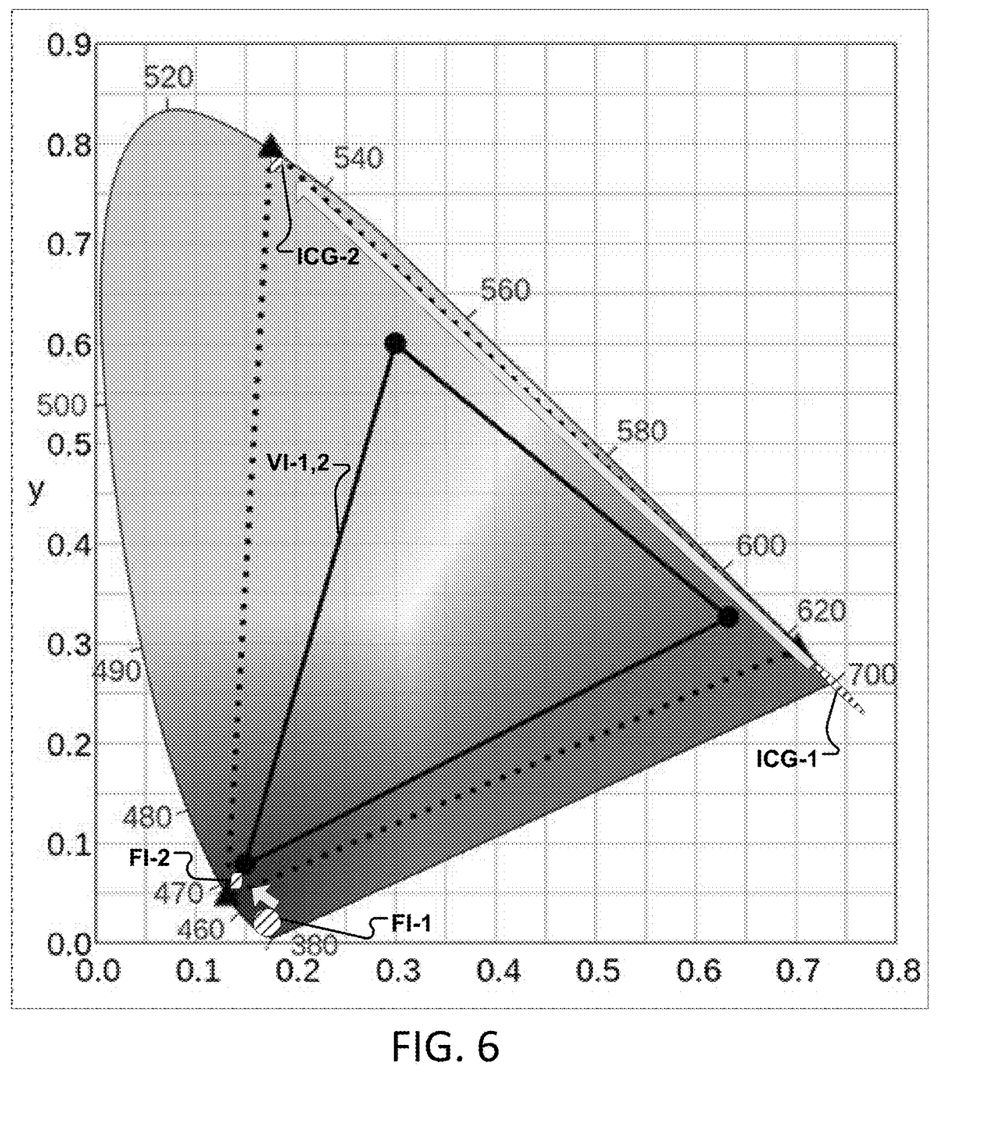
FIG. 6 shows an example color space diagram according to another embodiment in which two FI image signals are transformed to different color ranges of a single point, with the FI signal used to vary the intensity (luminance) of the color.

Referring to FIGS. 5-6, FIG. 5 shows an example color space diagram according to an embodiment in which two FI image signals are transformed to different color ranges having color variation therein. FIG. 6 shows an example color space diagram according to another embodiment in which two FI image signals are transformed to different color ranges of a single point, with the FI signal used to vary the intensity (luminance) of the color. In the embodiments of FIG. 6, transforming the second image stream to a first color range includes mapping an intensity range in the second image stream to an intensity range of a selected color, such as the primary green color shown as ICG-2. Similarly, transforming the third image stream includes mapping an intensity range in the second image stream to an intensity range of another selected color, such as the primary blue color shown as FI-2. In some implementations, mapping the FI signal intensity range is done by creating a 3-channel signal from only the FI signal, for example for the ICG-2 signal, creating a BT-2020 RGB signal with the range (0, 768-1023, 0) where the 768-1023 range represents the original 8-bit (0-255) FI signal intensity range, applied only to the Green channel with Red and Blue kept at zero. A similar mapping may occur for the FI-1 signal by creating a BT-2020 RGB signal with the range (0, 0, 768-1023), using only primary blue to for FI-2. Other single colors may also be used as the first and second color ranges ICG-2 and FI-2. For example, pure purple (1023,0,1023) may be scaled with the FI signal intensity to provide the desired transform resulting in a purple image distinguishable from the VI-2 images for easy combination and display. Any other suitable single color outside the first color space (the VI-1,2 triangle in this embodiment) may be used to display the first and second color ranges. In cases where even more fluoresced light images are desired to be combined, such as 3 or 4, preferably distinguishable colors are chosen based on the considerations that they should be far from the VI-1,2 triangle, and far from each other. For example, pure green, pure blue, and pure purple may be used to show three FI image streams combined with a visual image stream VI-2. Or pure green, pure blue, and cyan (halfway between green and blue) may be employed. Further the intensity range may be scaled by any desired amount within the single color, such as to fill half the available variation, or may be adjusted down from having a top-of-range value of 1023 to avoid saturating the display toward white when combined with other colors of high saturation in the VI-2 image stream.

Referring to FIG. 5, the FI signals ICG-1 and FI-1 may also be transformed to a color range including multiple colors along a band, such as the depicted bands of color ICG-2 and FI-2. Such a transformation may assist in the user in distinguishing values in the transformed FI images when they are combined with the VI-2 image and displayed. For example, a transform may vary the color of ICG-2 in the depicted band from blue-green toward pure green, as the intensity of the original ICG-1 image signal increases. This may be done at a fixed luminance (light intensity) value of ICG-2, or may also be done along with an intensity variation of the ICG-1 color as well. In one version, the first fluoresced light ICG-1 is from an indocyanine green (ICG) fluorescing agent, and in the transformation the first color range inside the second color space and outside the first color space includes the first color range consisting essentially of a green or multiple shades of green. In another version, the first fluoresced light ICG-1 is transformed to a color range outside the first color space consisting essentially of shades of green, shades of blue, or shades of both green and blue. To create such a range, the use of pure primaries of green and blue primaries of the second color space is not absolutely necessary, and non-zero values of the red primary, or combinations of other color primaries in other color spaces that include a yellow primary, for example, may be used as long as the displayed colors of the range are outside the first color space and show colors perceived to be shades of green and or shades of blue as discussed. In such a version, the ICG-2 color range shown in the diagram may stretch from the green range in which it is depicted all the way to the blue range where the FI-2 color range is currently depicted. A similar scheme may be used for FI-2, varying FI-2 through multiple shades of blue from a selected green-blue color, or from a selected red-blue color, toward pure blue as the intensity of FI-1 increases. Color ranges such as a range centered along the red-to-blue edge of the second color space (the dotted triangle) may also be used for conversion of one of the FI image streams.

Preferably, the first color space is an 8-bit color space and the second color space is a BT-2020 compliant 10-bit or 12-bit color space, with the video encoder circuitry 80 (FIG. 1) or process (319) configured to encode the combined image stream to a BT-2020 compliant video format for display on a BT-2020 compliant 4k or UHD monitor. In some cases the full image resolution of BT-2020 UHD may not be used on the monitor, while the full color range is used.

Figure 7:
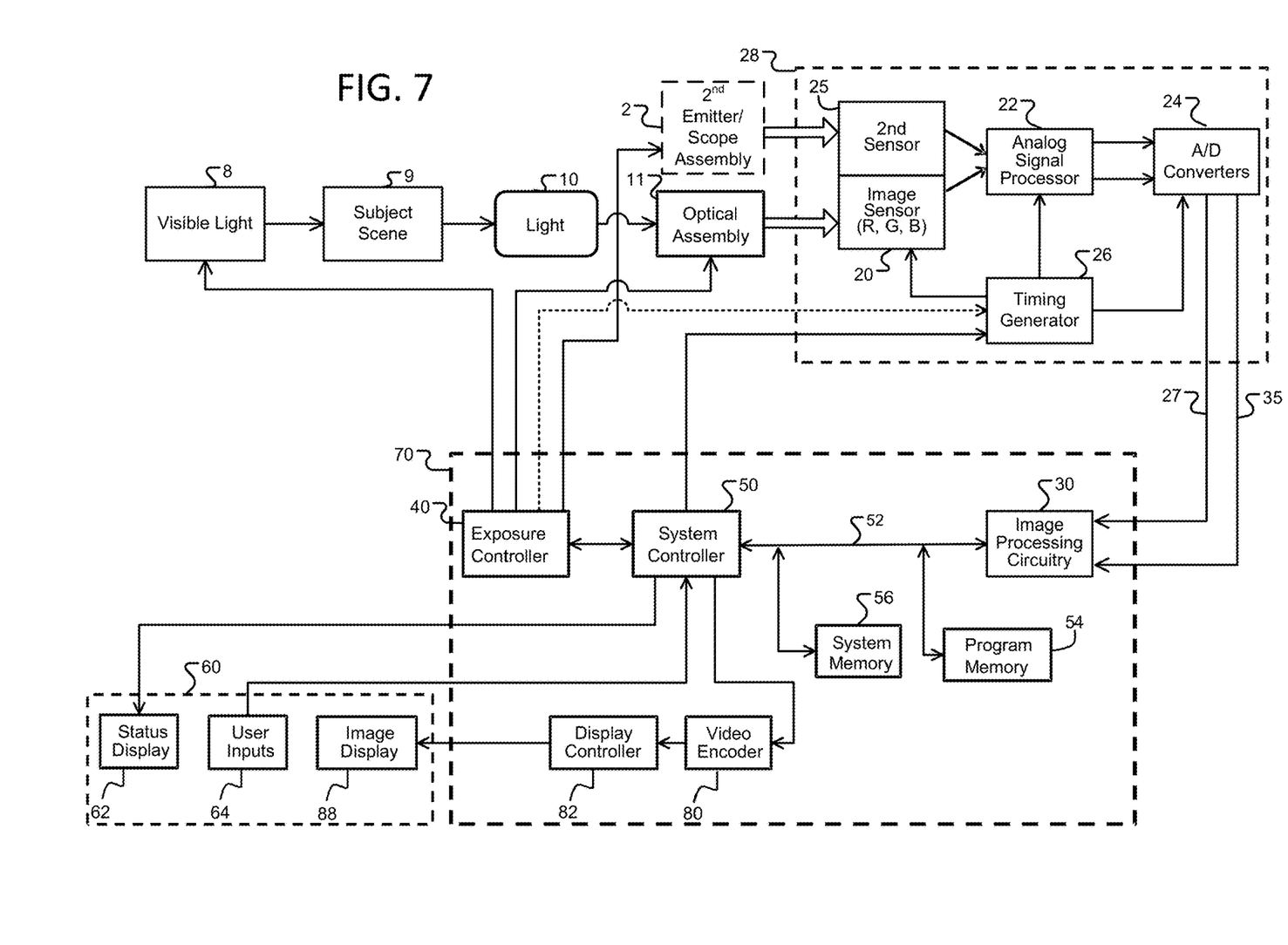
FIG. 7 is a hardware block diagram of an example medical data capture system according to additional example embodiments.

While fluorescence imaging is combined with reflected light imaging in some versions, this is not limiting and in other versions other types of images may be combined with the visible light images. FIG. 7 describes other embodiments in which other sensor data is used to produce image data that is combined with a visual reflected light image according to the techniques herein.

FIG. 7 is a hardware block diagram of an example medical data capture system according to additional example embodiments. The block diagram is similar to that of FIG. 1 with regard to the reflected light sensing and image processing, but instead of fluorescence imaging, the system includes a second sensor 25 to provide data which is used to create a second sensor data signal 35 that is combined with the reflected light image data 27 in a manner similar to that employed with fluorescence imaging data signals herein. The second sensor 25 may be a variety of medical sensors that can provide data to be used along with a reflected light image to further diagnose or examine target tissues. Second sensor 25 may also be an infrared or near-infrared sensor detecting infrared or near-infrared light across a desired spectrum. In one embodiment, second sensor 25 is an optical coherence tomography (OCT) sensor, sensing light from an OCT scope assembly that is integrated with the reflected light scope. Further, second sensor 25 may also be an acoustic sensor such as an ultrasonic pulse or other ultrasound sensor, detecting sound emitted toward and reflected from target tissue using an ultrasound device such as an endoscopic ultrasound device. In versions where second sensor 25 cannot use the same optical assembly 11 as image sensor 20, a second emitter or scope assembly 2 is provided feeding sound, light, or other detectable signals from the subject scene 9 to second sensor 25. Second emitter or scope assembly 2 is preferably integrated in the same scope housing as optical assembly 11, but may be in a separate detachable housing. In such cases, the two housings are preferably designed to be rigidly attached and detached by the user in such a manner that the second sensor has a common field of view with the image sensor, though it may be larger, smaller, or deeper than the field of view of sensor 20. The construction of infrared, OCT, and ultrasonic pulse or ultrasound devices is known in the art and will not be further described here to avoid obscuring the important elements. Examples of such devices are described in U.S. Pat. No. 8,858,426 (ultrasound endoscope with image pickup), and U.S. Pat. No. 6,507,747 (optical imaging probe including spectroscopic imaging probe and OCT imaging probe elements).

Second sensor 25 may be an array or a single sensor, or a directional sensor that is scanned along a field of view. Second sensor 25 and its accompanying scope assembly and emitters 2, if any, are aligned with image sensor 20 such that second sensor 25 has field of view or sensing substantially the same as or contained within the field of view for image sensor 20, although second sensor 25 may detect signals at a penetrating depth through opaque tissue, and therefore provide a field of sensing that is deeper in a Z direction, but still at a range of view or sensing (X,Y) substantially shared with image sensor 20.

Data from second sensor 25 is processed through analog signal processor 22 and converted to a digital data stream by A/D converters 24. In versions where image data is sensed directly, the data signal 35 transmitted to image processing circuit 30 is an image stream. In some versions, data from sensor 25 may need further processing, such as FFTs, or other transforms to create the desired image stream from second sensor 25 data. In any event, an image stream is created based on second sensor data signal 35 and is then displayed combined with the reflected light image stream according to the techniques herein. For example, in FIG. 2 the second sensor data signal 35 may be processed through signal processing circuitry similar to that provided for fluorescent data signal 29. For each possible variation of second sensor 25, a corresponding method is provided for transforming information representing the data detected by second sensor 25 to a color range outside the color space of the first image stream. In some cases the data transformed second sensor data may represent detected light or detected light difference signals, but in others it may represent ultrasonic signals. As such, the pre-transformed data of the second sensor 25 may not be represented on the chromaticity color chart, or may be an intensity level often represented as a grayscale image which may be placed, for example, at the white level of the chart with the intensity variation representing a grayscale variation from white. A method for processing the second sensor data is also shown in FIG. 3 where process block 302 may receive the second sensor data and process and transform it to the second data format and desired color range according to the methods described above. As discussed with respect to the FI image processing, the frame rate of images from second sensor 25 may vary from that of image sensor 20, and so the process may repeat frames or interpolate frames to pad the second image stream and synchronize the combined images in time. Before this, process block 304 may further conduct transforms to create the desired image from sensor data such as OCT data. Process block 304 may also conduct steps to align the images. The desired color range of the transform at block 306 may be selected according to any of the discussion above.

The techniques discussed above may be implemented in a variety of hardware designs, and signal processing software designs. The design should be conducted considering the need for real-time image display, that is, to minimize lag on the display as the scope is moved by medical personnel. The parallel hardware design of FIG. 2 is therefore advantageous because it adds little processing time to the slower parts of the system, that is the image processing steps conducted on the full color visible image or the combined image.

It can also be understood, after appreciating this disclosure, that the techniques herein may be employed in other fields that include combining fluorescent imagery with visible light imagery, such as microscopy.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An imaging scope system, comprising:
a light source configured to direct visible light and fluorescent excitation light toward a subject scene;
an optical assembly configured to direct received light from the subject scene toward an image sensor assembly;
the image sensor assembly including at least one image sensor, the image sensor assembly capable of detecting visible light and first fluoresced light from the subject scene and producing at least one output signal response;
image forming circuitry configured to receive the at least one output signal and produce a first image stream including visible light images having a first color space and a second image stream representing the first fluoresced light;
image processing circuitry configured to:
(a) convert a format of the first image stream into a second data format having a second color space larger, in terms of the range of colors, than the first color space, while preserving color space content of the first image stream;
(b) format the second image stream to the second data format and transform the second image stream to a first color range inside the second color space and outside the first color space;
(c) combine the converted first image stream and the transformed second image stream to produce a combined image stream; and
video encoder circuitry configured to encode the combined image stream to a video encoding format configured for display on an electronic display capable of displaying the second color space.

2. The imaging scope system of claim 1 in which the first image stream expresses the first color space with a first bit depth, and the converted image stream expresses the second color space with a second bit depth larger than the first bit depth.

3. The imaging scope system of claim 1 in which transforming the second image stream to a first color range comprises mapping an intensity range in the second image stream to an intensity range of a selected color.

4. The imaging scope system of claim 1 in which the second image stream has a bit depth expressing intensity variation of the detected first fluoresced light, said bit depth smaller than the bit depth of the second color space, and in which the image processing circuitry further comprises circuitry operable to transforming from second image stream by adding an intensity variation in the second image stream to a base value for a single selected color in the second color space.

5. The imaging scope system of claim 1 in which transforming the second image stream to a first color range further comprises mapping an intensity range in the second image stream to the first color range.

6. The imaging scope system of claim 1 in which the first fluoresced light is from an indocyanine green (ICG) fluorescing agent and the first color range consists essentially of a green or multiple greens.

7. The imaging scope system of claim 1 in which:
the image sensor assembly is further capable of detecting second fluoresced light at a spectrum different from that of the first fluoresced light and produce a second fluoresced light signal in response;
the image forming circuitry is further configured to produce a third image stream representing the second fluoresced light; and
the image processing circuitry is further configured to format the third image stream to the second data format and transform the third image stream to a second color range inside the second color space and outside the first color space and outside the first color range, and combine the third image stream with the first and second image streams.

8. The imaging scope system of claim 1 in which the image processing circuitry further includes first processing circuitry for processing the first image stream and second processing circuitry operating in parallel with the first processing circuitry for processing the second image stream, the first and second processing circuitry both connected to image combining circuitry, and further in which the first and second processing circuitry comprise independent parallel circuits in a field programmable gate array (FPGA).

9. The imaging scope system of claim 1 in which converting the format of the first image stream is done by accessing a lookup table containing a set of first pixel values for the pre-converted first images and an associated set of second pixel values for converted first images.

10. The imaging scope system of claim 1 in which the first color space is an 8-bit color space and the second color space is a BT-2020 compliant 10-bit or 12-bit color space, and in which and transmitting the combined stream encoded for a display capable of displaying the second color space further comprises encoding the combined image stream to a BT-2020 compliant video format.

11. A method of transforming information representing detected light, the method comprising:
(a) receiving a first image stream produced from detected visible light and formatted in a first bit depth expressing a first color space of visible light;
(b) receiving a second image stream produced from detected first fluoresced light;
(c) converting the format of the first image stream into a second color space format having a second bit depth larger than the first bit depth, the second color space larger, in terms of the range of colors, than the first color space, while preserving color space content of the first image stream;
(d) transforming the second image stream to a portion of the second color space outside the first color space;
(e) combining the converted first image stream and the transformed second image stream into a combined image stream and encoding the combined stream formatted for a display capable of displaying the second color space.

12. The imaging scope system of claim 1 in which transforming the second image stream to a first color range comprises mapping an intensity range in the second image stream to an intensity range of a selected color.

13. The method of claim 11 in which transforming the second image stream to a first color range inside the second color space and outside the first color space further comprises mapping an intensity range in the second image stream to the first color range.

14. The method of claim 11 in which the first fluoresced light is from an indocyanine green (ICG) fluorescing agent, and in which transforming the second image stream to a first color range inside the second color space and outside the first color space further includes the first color range consisting essentially of multiple shades of green, multiple shades of blue, or multiple shades of green and blue.

15. The method of claim 11 further comprising:
receiving a third image stream produced from detected second fluoresced light at a spectrum different from that of the first fluoresced light;
formatting the third image stream to the second data format and transforming the third image stream to a second color range inside the second color space and outside the first color space, and outside the first color range;
combining the third image stream with the first and second image streams.

16. The method of claim 11 in which the first color space is an 8-bit color space and the second color space is a BT-2020 compliant 10-bit or 12-bit color space, and in which encoding the combined image stream includes encoding to a BT-2020 compliant video format.

17. The method of claim 11 further comprising detecting the first fluoresced light and producing the second image stream based on the detected first fluoresced light.

18. The method of claim 11 in which converting the format of the first image stream is done by accessing a lookup table containing a set of first pixel values for pre-converted first images and an associated set of second pixel values for converted first images.

19. The method of claim 11 in which transforming from second image stream further comprises adding an intensity variation in the second image stream to a base value for a single selected color in the second color space.

20. The method of claim 11 in which in which transforming the second image stream further comprises accessing a lookup table containing a set of input pixel values for pre-transformed second images and an associated set of output pixel values for transformed second images.

21. The method of claim 11 in which transforming from second image stream further comprises adding a transparency level to the second image stream, and in which combining the converted first image stream and the transformed second image stream further comprises alpha blending in which the transparency level is used as the alpha level for the second image stream.

22. A method of transforming information representing detected sensor data, the method comprising:
(a) receiving a first image stream produced from reflected light and formatted in a first bit depth expressing a first color space of visible light;
(b) receiving a second image stream produced from detected second sensor data having an angle of sensing at least substantially shared with an angle of view of the first image stream;
(c) converting the format of the first image stream into a second color space format having a second bit depth larger than the first bit depth, the second color space larger, in terms of the range of colors, than the first color space, while preserving color space content of the first image stream;
(d) transforming the second image stream to a portion of the second color space outside the first color space;
(e) combining the converted first image stream and the transformed second image stream into a combined image stream and encoding the combined stream formatted for a display capable of displaying the second color space.

23. The method of claim 22 in which the second sensor data is received from one of an ultrasonic sensor, an infrared sensor, and a near-infrared sensor.

24. A camera control unit (CCU) configured to receive a first image stream including visible light images having a first color space and a second image stream representing detected fluoresced light, the CCU comprising image processing circuitry configured to:
(a) convert a format of the first image stream into a second data format having a second color space larger, in terms of the range of colors, than the first color space while preserving color space content of the first image stream;
(b) format the second image stream to the second data format and transform the second image stream to a first color range inside the second color space and outside the first color space; and
(c) combine the converted first image stream and the transformed second image stream to produce a combined image stream.

25. The camera control unit of claim 24 further comprising video encoder circuitry configured to encode the combined image stream to a video encoding format configured for display on an electronic display capable of displaying the second color space.

* * * * *